United States Patent
Zhang et al.

(10) Patent No.: US 7,759,150 B2
(45) Date of Patent: Jul. 20, 2010

(54) NANOROD SENSOR WITH SINGLE-PLANE ELECTRODES

(75) Inventors: Fengyan Zhang, Camas, WA (US); Bruce D. Ulrich, Beaverton, OR (US); Wei Pan, Vancouver, WA (US); Lawrence J. Charneski, Vancouver, WA (US); Sheng Teng Hsu, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 654 days.

(21) Appl. No.: 11/805,011

(22) Filed: May 22, 2007

(65) Prior Publication Data

US 2008/0290431 A1 Nov. 27, 2008

(51) Int. Cl.
*H01L 21/00* (2006.01)

(52) U.S. Cl. .............. 438/48; 438/56; 438/57; 438/66; 438/73; 438/80; 438/85; 257/419; 257/E21.09; 257/E29.324

(58) Field of Classification Search .................. None
See application file for complete search history.

(56) References Cited

U.S. PATENT DOCUMENTS 7,640,789 B2 * 1/2010 Kim et al. ............ 73/31.06

| | | | |
|---|---|---|---|
| 2006/0292839 A1 * | 12/2006 | Yi et al. | 438/570 |
| 2008/0246961 A1 * | 10/2008 | Zhang et al. | 356/317 |
| 2008/0264479 A1 * | 10/2008 | Harris et al. | 136/255 |
| 2010/0012919 A1 * | 1/2010 | Park et al. | 257/9 |

FOREIGN PATENT DOCUMENTS

| JP | 2003-301283 | 10/2003 |
|---|---|---|
| JP | 2007-171207 | 7/2007 |

* cited by examiner

*Primary Examiner*—Zandra Smith
*Assistant Examiner*—Khanh B Duong
(74) *Attorney, Agent, or Firm*—Law Office of Gerald Maliszewski; Gerald Maliszewski

(57) ABSTRACT

A nanorod sensor with a single plane of horizontally-aligned electrodes and an associated fabrication method are provided. The method provides a substrate and forms an intermediate electrode overlying a center region of the substrate. The intermediate electrode is a patterned bottom noble metal/Pt/Ti multilayered stack. $TiO_2$ nanorods are formed over the substrate and intermediate electrode, and a $TiO_2$ film may be formed overlying the $TiO_2$ nanorods. The $TiO_2$ nanorods and $TiO_2$ film are formed in-situ, in the same process, by varying the substrate temperature. In other aspects, the $TiO_2$ film is formed between the nanorods and the intermediate electrode. In yet another aspect, the $TiO_2$ film is formed both above and below the nanorods. A single plane of top electrodes is formed overlying the $TiO_2$ film from a top noble metal/Pt/Ti multilayered stack overlying the $TiO_2$ film, which has been selectively etched to form separate top electrodes.

14 Claims, 6 Drawing Sheets

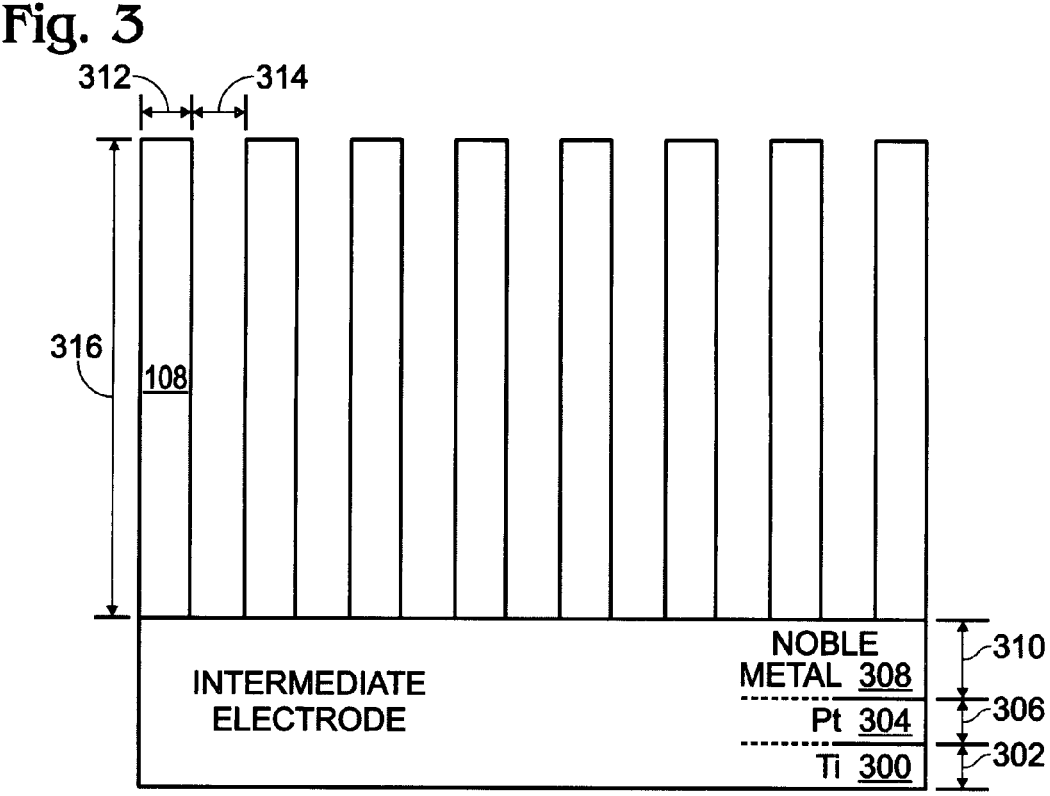
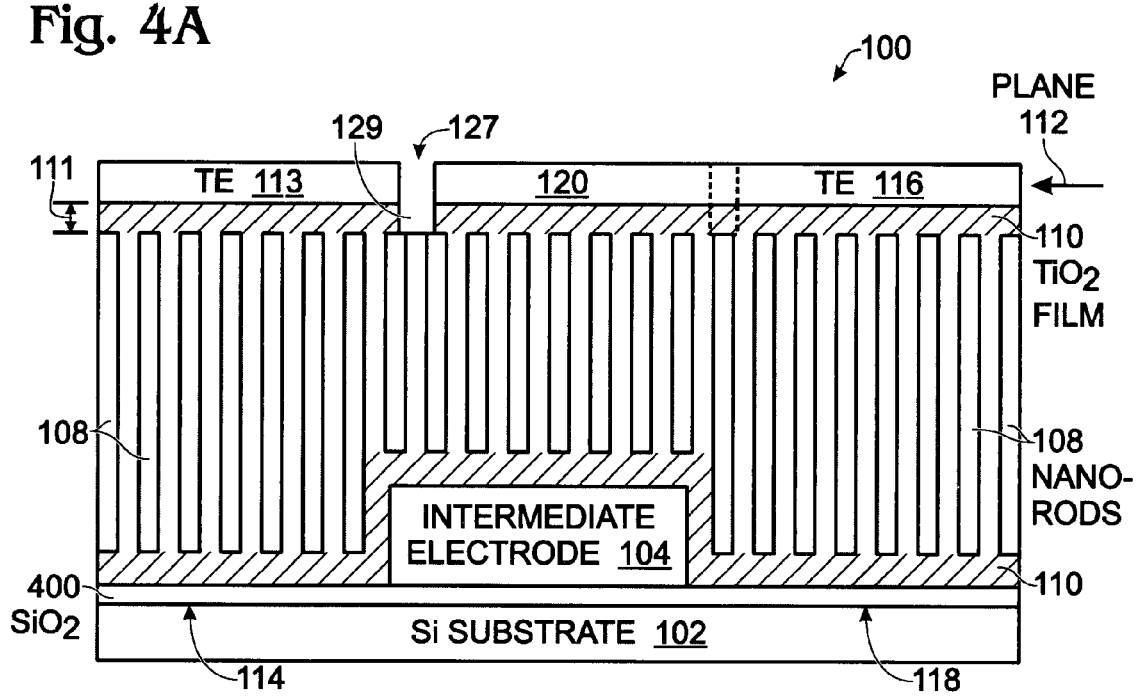

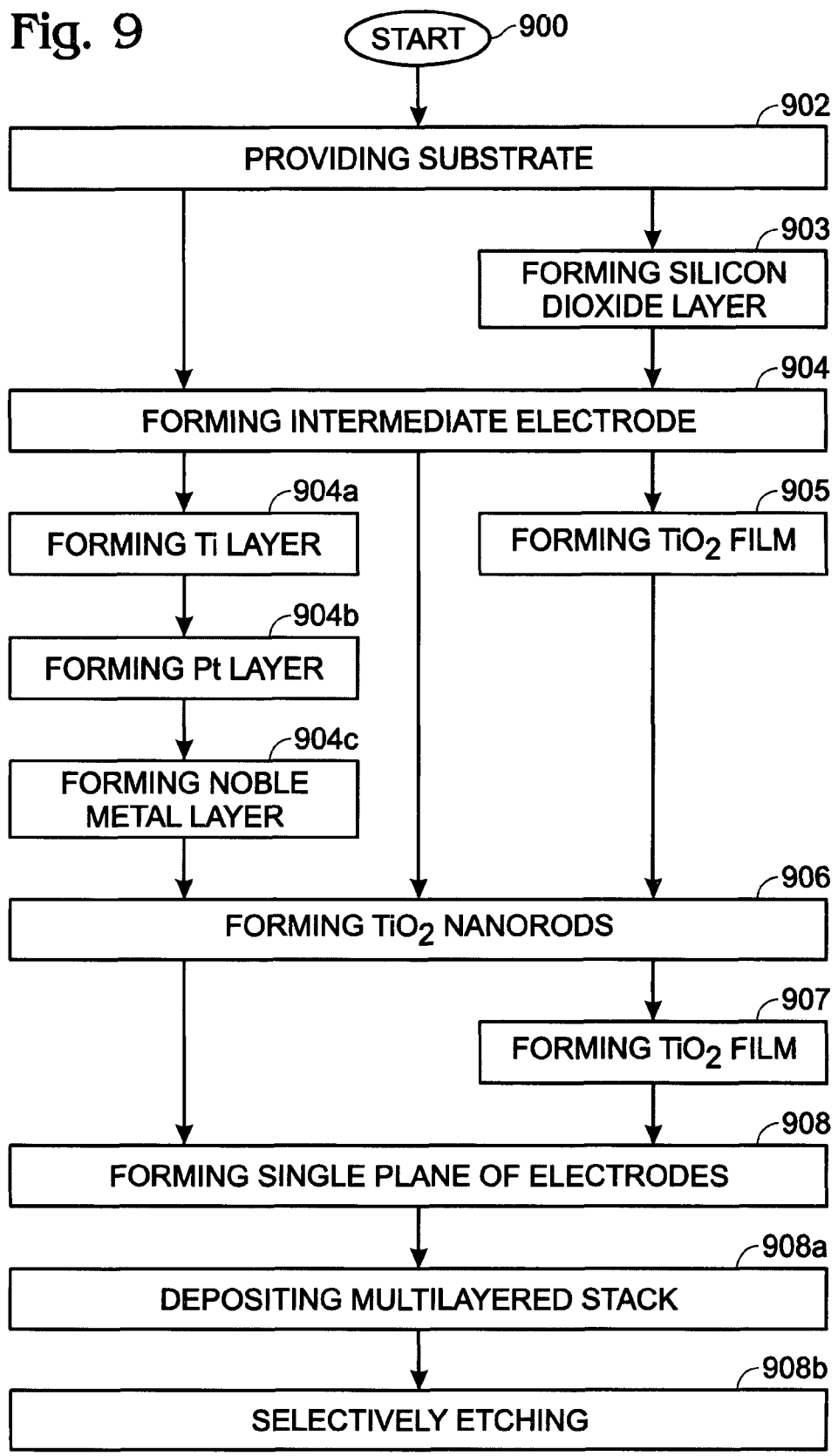

NANOROD SENSOR WITH SINGLE-PLANE ELECTRODES

BACKGROUND OF THE INVENTION

1. Field of the Invention

This invention generally relates to integrated circuit (IC) fabrication and, more particularly, to a nanorod sensor with both electrodes formed on the top surface, and a process for fabricating the nanorod sensor.

2. Description of the Related Art

Recently, the fabrication of nanowires has been explored due to its potential importance as a building block in nano, microelectromechanical (MEM), and nanoelectromechanical NEM device applications. For example, researchers associated with Charles Lieber have reported the synthesis of a variety of semiconductor nanowires made from materials such as silicon (Si), Si-germanium (SiGe), InP, and GaN, for use in building nano-computing system. Other groups have also reported using templates structures to grow metallic nanowires made of materials such as Ni, NiSi, Au, and Pt. Metallic nanowires can be used as interconnections and the sharp tips of the nanowire make them effective for field emission purpose. Metal oxide nanowires/rods/tubes have been used in gas sensor applications due to their advantages of low power, low cost, high sensitivity, and high stability.

One key problem has been with the integrity of nanorod sensors, as the nanorods are inherent fragile. As a result, designs have been limited to less effective two-dimensional (2D) nanorod fields. However, even 2D nanorod gas sensors have been difficult to fabricate in large scale production with reproducibility.

It would be advantageous if a three-dimensional (3D) nanorod gas sensor structure could be made using conventional IC processes.

SUMMARY OF THE INVENTION

The present invention describes a 3D nanorod gas sensor structure that is compatible with conventional IC processes for ease of large scale production. By integrating different sensing elements together, such as different materials, different coatings, and different film stacks, greater and varied sensitivities may be obtained for e-nose applications.

Accordingly, a method is provided for fabricating a nanorod sensor with a single plane of horizontally-aligned electrodes. The method provides a substrate and forms an intermediate electrode overlying a center region of the substrate. The intermediate electrode is a patterned bottom noble metal/Pt/Ti multilayered stack. $TiO_2$ nanorods are formed over the substrate and intermediate electrode, and a $TiO_2$ film may be formed overlying the $TiO_2$ nanorods. The $TiO_2$ nanorods and $TiO_2$ film are formed in-situ, in the same process, by varying the substrate temperature. In other aspects, the $TiO_2$ film is formed between the nanorods and the intermediate electrode. In yet another aspect, the $TiO_2$ film is formed both above and below the nanorods. A single plane of top electrodes is formed overlying the $TiO_2$ film from a top noble metal/Pt/Ti multilayered stack overlying the $TiO_2$ nanorods, which has been selectively etched.

More particularly, the top noble metal/Pt/Ti multilayered stack is etched to form a first top electrode overlying a first region of the $TiO_2$ film and a second top electrode overlying a second region of the $TiO_2$ film. An interdigital electrode is also formed overlying the intermediate electrode, interposed between the first and second top electrodes. The interdigital electrode has a first section connected to the first top electrode and a second section connected to the second top electrode.

Additional details of the above-described method, and a nanorod sensor with a single plane of horizontally-aligned electrodes, are described below.

BRIEF DESCRIPTION OF THE DRAWINGS

FIG. 3 is a detailed depiction of the bottom noble metal/Pt/Ti multilayered stack of FIG. 1.

FIGS. 4A and 4B are partial cross-sectional views of variations of the nanorod sensor of FIG. 1.

FIG. 9 is a flowchart illustrating a method for fabricating a nanorod sensor with a single plane of horizontally-aligned electrodes.

DETAILED DESCRIPTION

Figure 1:
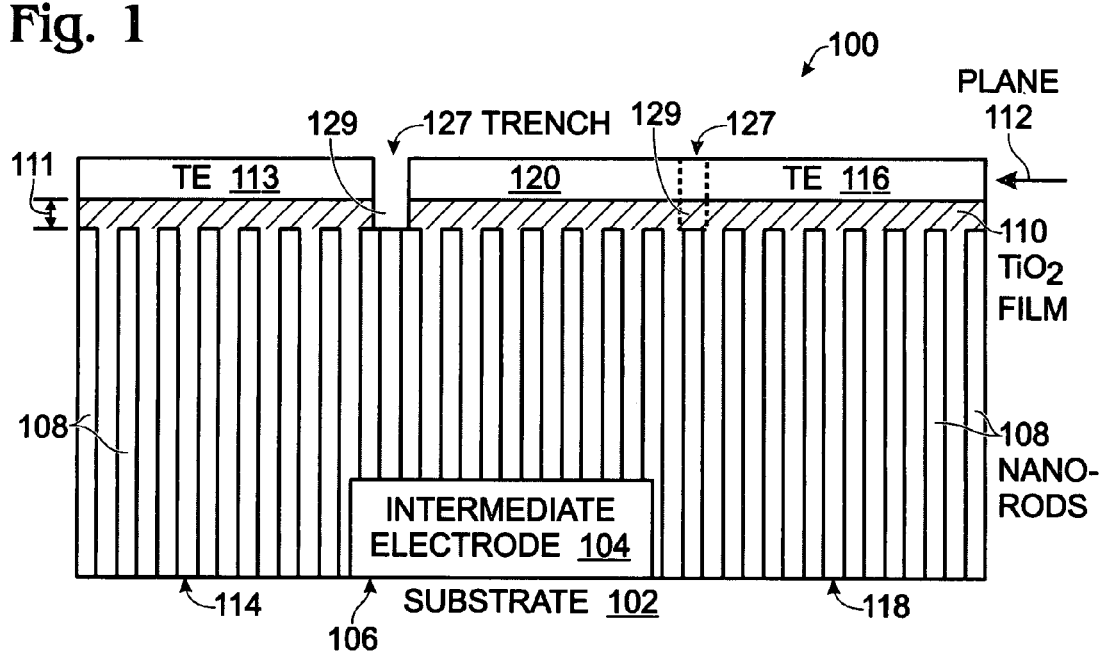
FIG. 1 is a partial cross-sectional view of a nanorod sensor with a single plane of horizontally-aligned electrodes.

FIG. 1 is a partial cross-sectional view of a nanorod sensor with a single plane of horizontally-aligned electrodes. The sensor 100 comprises a substrate 102. The substrate 102 may be a material such as Si, glass, plastic, or polyimide. However, there are many unnamed flexible and inflexible substrate materials that would enable the sensor. An intermediate electrode 104 is formed from a patterned bottom noble metal/Pt/Ti multilayered stack overlying a center region 106 of the substrate 102. $TiO_2$ nanorods 108 overlie the intermediate electrode. Nanorods 108 may also be formed over the substrate surfaces adjacent the intermediate electrode 104, as shown. Although not connected between conductive electrodes, the nanorods adjacent the intermediate electrode 104 may be used to provide support for the top electrodes. In one aspect, a $TiO_2$ film 110 overlies the $TiO_2$ nanorods 108. For example, the $TiO_2$ film 110 has a thickness 111 in a range of 10 nm to 2 um. A single plane 112 of top electrodes overlies the $TiO_2$ nanorods 108.

Figure 2:
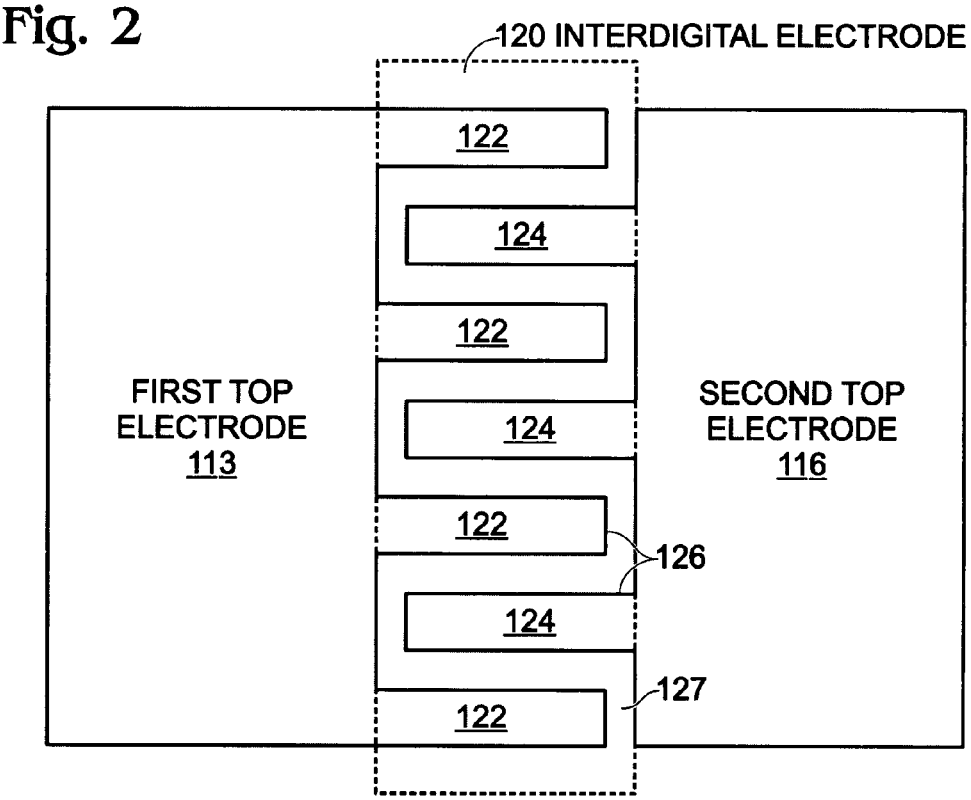
FIG. 2 is a plan view of the sensor of FIG. 1, as seen from the top.

FIG. 2 is a plan view of the sensor of FIG. 1, as seen from the top. The single plane of top electrodes includes top electrodes formed from a patterned top noble metal/Pt/Ti multilayered stack. More explicitly, a first top electrode (TE) 113 overlies a first region of the substrate (114, see FIG. 1). A second top electrode 116 overlies a second region 118 of the substrate. An interdigital electrode 120 overlies the intermediate electrode 104, and is interposed between the first top electrode 112 and the second top electrode 116. The interdigital electrode 120 has a first section 122 connected to the first top electrode 112 and a second section 124 connected to the second top electrode 116. As noted above, the $TiO_2$ nanorods 108 overlie the substrate 102 adjacent the intermediate electrode 104, overlying the first and second regions 114/118 of substrate.

In one aspect as shown, the interdigital electrode 120 includes interdigital fingers 126 and a boundary region 127 separating the first section 122 from the second section 124. However, other patterns could be used to differentiate the first and second sections 122/124. The $TiO_2$ film 110 includes etched trenches 129 underlying the interdigital electrode boundary region 127. In some aspects, it is desirable that the trenches 129 are etched through the nanorods 108, extending all the way to the intermediate electrode 104, and in some circumstances to the substrate 102.

FIG. 3 is a detailed depiction of the bottom noble metal/ Pt/Ti multilayered stack of FIG. 1. Although not specifically shown in FIG. 3, the details of the bottom stack apply equally well to the top noble metal/Pt/Ti multilayered stack. A Ti layer 300 has a thickness 302 in a range of 10 to 100 nanometers (nm). A Pt layer 304 overlying the Ti layer 302 has a thickness 306 in a range of 10 to 100 nm. A noble metal layer 308 overlying the Pt layer 304 has a thickness 310 of 100 nm to 1 micrometer. Typically, the top and bottom noble metal/ Pt/Ti multilayered stacks use a noble metal such as Au, Ir, Pt, or Ru. It is desirable that the electrodes do not react with the ambient gas and the sensing element. Typically, the above-mentioned noble metals can be used in a gas sensor electrode, regardless of the sensing element material. The Pt/Ti are adhesion promotion layers that works well with the $TiO_2$ nanorods. However, these adhesion promotion layers are nor always required. Other materials are known in the art that can be used to promote adhesion, without changing the sensing properties of the sensor.

Also seen in this detail, the $TiO_2$ nanorods 108 have a length 316 in the range of 10 nm to 10 micrometers (um), a diameter 312 in a range of 10 nm to 1 um, and a spacing 314 between nanorods in a range of 1 nm to 1 um.

Figure 4B:
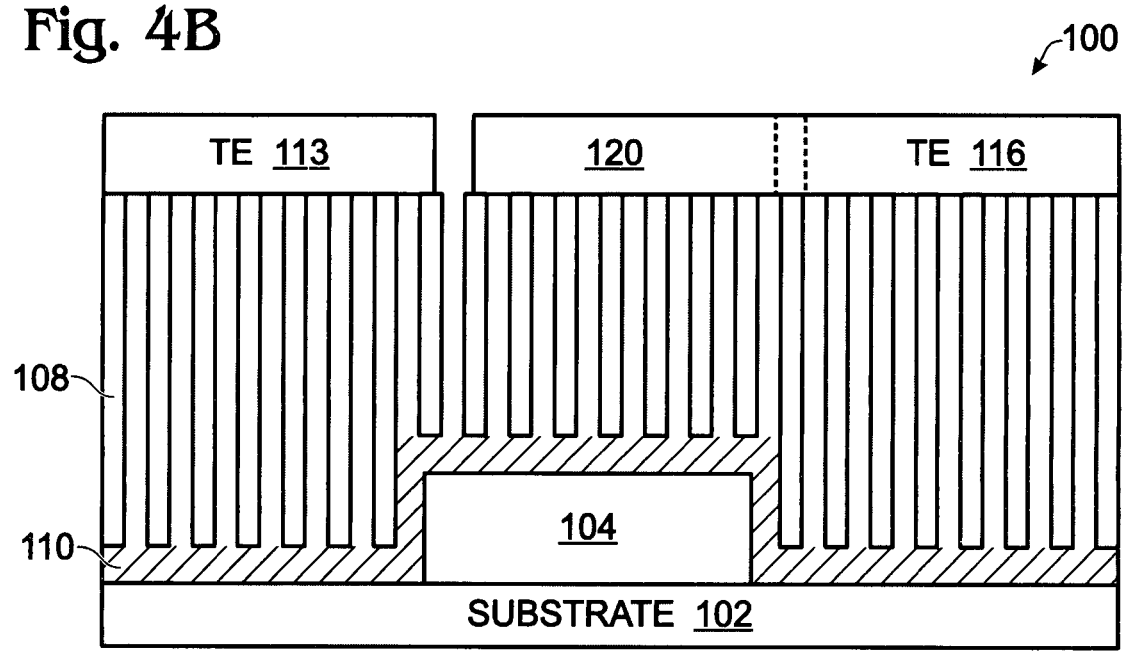

FIGS. 4A and 4B are partial cross-sectional views of variations of the nanorod sensor of FIG. 1. In FIG. 4A, the substrate 102 is a Si, and a silicon dioxide layer 400 overlies the substrate. If other semi-conductive type substrate materials are used, the sensor would also benefit from an electrical insulator layer such silicon dioxide. Other insulator materials are well known in the art. As shown, the $TiO_2$ film 110 overlies the nanorods 108 (as in FIG. 1), but also underlies the nanorods. That is, the film 110 is interposed between the nanorods 108 and the intermediate electrode 104, and interposed between the nanorods 108 and the top electrodes 112 and 116, and the interdigital electrode 120. Optionally but not shown, the trenches 129 may extend into the nanorods 108, or even into the nanorods and through the bottom $TiO_2$ film.

As shown in FIG. 4B, the TiO2 film 110 is interposed between the TiO2 nanorods 108 and the intermediate electrode 104, as well as interposed between the nanorods and the substrate 102. Etched trenches 129 are formed in the top TiO2 film 110. Optionally but not shown, the trenches 129 may extend into the nanorods 108, or even into the nanorods and through the bottom $TiO_2$ film.

The nanorods in the above-described figures may have a circular cross-section. In other aspects the nanorods may have a square, triangular, or oval shape. Further, is some aspects not shown, there may be a cavity or hollow region in the center of the core. Alternately, a nanorod may be referred to as a nanowire, nanostructure, or nanotube.

Functional Description

Figure 5:
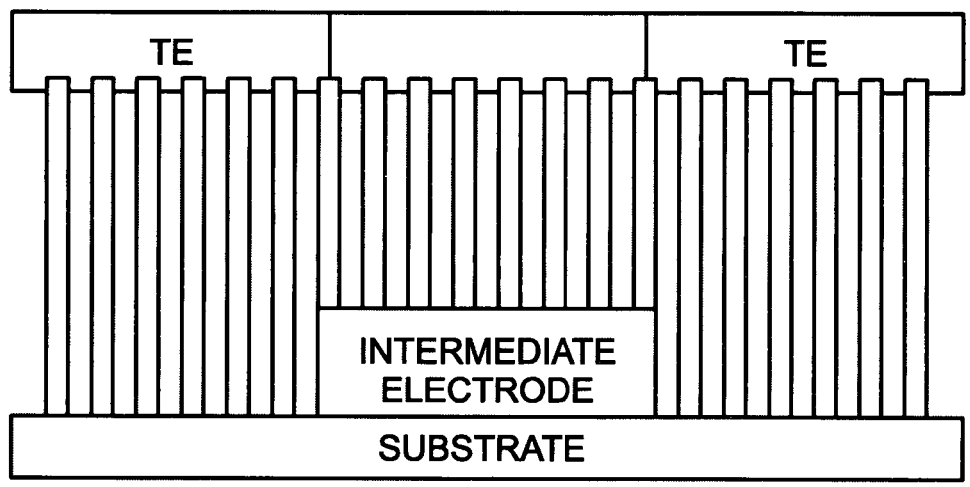
FIG. 5 is an alternate cross-sectional depiction of the nanorod sensor of FIG. 1.

FIG. 5 is an alternate cross-sectional depiction of the nanorod sensor of FIG. 1. If the substrate is Si, it may be coated with $SiO_2$. Alternatively, a glass or flexible substrate can also be used as the substrate.

Figure 6:
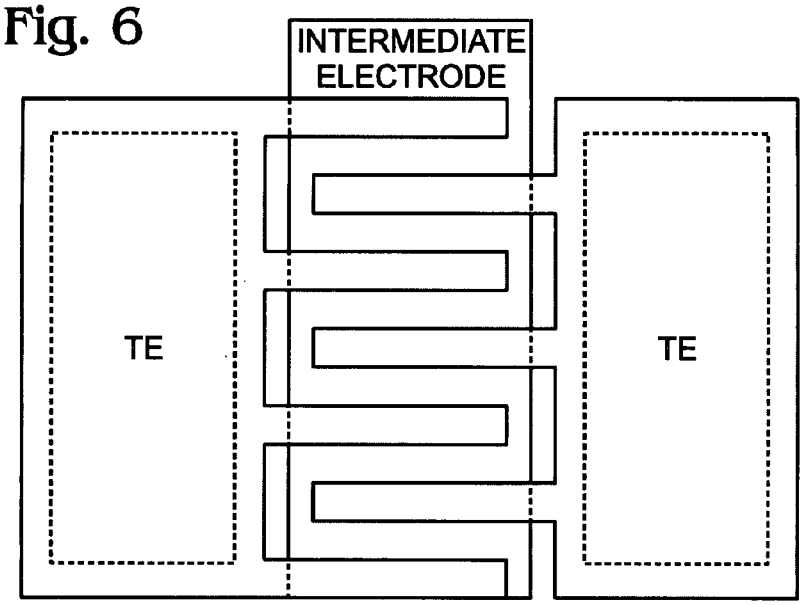
FIG. 6 is a plan view showing the relative positions of the top electrodes with respect to the intermediate electrode.

FIG. 6 is a plan view showing the relative positions of the top electrodes with respect to the intermediate electrode. Note: the interdigital electrode, $TiO_2$ nanorods, and $TiO_2$ film are invisible in this view. In this example, the intermediate electrode is a Au/Pt/Ti multilayer with layer thicknesses of 350 nm, 50 nm, and 50 nm, respectively. The intermediate electrode may be patterned using a dry etching process. Then, $TiO_2$ nanorods are grown on the Au surface and the other areas of the substrate. The growth conditions are as follows: the substrate temperature is maintained at 200-800° C.; the pressure is in the range of 1 Torr to 1 Atmosphere; the precursor is Ti isopropoxide (Ti $(OC_3H_7)_4$). Both the precursor and the transport line are maintained at 20-80° C. The reaction gas is $O_2$ and the carrier gas is Ar. Alternatively, other inert gas such as Ar and $N_2$ can also be used as the reaction gases. The chamber is initially pumped down to below 1 mtorr, and then Ar fills the chamber to the required growth pressure. The carrier gas is introduced into the growth chamber with the flow rate of 10-100 SCCM.

In order to prevent the shorting between the intermediate electrode and top electrodes, a $TiO_2$ thin film may deposited on top, underneath, or both on top and underneath the nanorods array.

The growth temperature for the $TiO_2$ thin film is in the range of 250-350° C. (to obtain anatase film) or 600° C.-800° C. (to obtain rutile phase). The growth temperature for the $TiO_2$ nanorods is in the range of 350-600° C. Anatase is one of the three mineral forms of titanium dioxide, the other two being brookite and rutile. Anatase phase $TiO_2$ is found as small, isolated and sharply developed crystals, and like rutile, it crystallizes in the tetragonal system. Although the degree of symmetry is the same for both phases, there is no relation between the interfacial angles of the two minerals, except, in the prism-zone of 45° and 90°. The common pyramid of anatase, parallel to the faces of which there are perfect cleavages, has an angle over the polar edge of 82° 9', the corresponding angle of rutile being 56° 52½'.

There are also differences between the physical characters of anatase and rutile; the former is not quite so hard (H=5½-6) or dense (specific gravity 3.9), and it is optically negative. Rutile is optically positive. The luster of anatase is even more strongly adamantine or metallic-adamantine than that of rutile. Rutile has among the highest refractive indices of any known mineral and also exhibits high dispersion.

After the metal oxide layer deposition, the Au/Pt/Ti multilayer top electrode is deposited on the surface of the nanorods. The thicknesses of the layers are 350 nm, 50 nm, and 50 nm, respectively. Then, dry etching is used to pattern a cross fingered top-to-top electrode structure. When $TiO_2$ thin film is interposed between the TiO2 nanorods and top electrode, the etching process is continued, to etch through the $TiO_2$ thin film. Preferably, the etch continues through the nanorods to the bottom substrate or intermediate electrode. It should be noted that sensors may also be made from other nanorod materials, such as $SnO_2$, $In_2O_3$, ZnO, $WO_3$, $MoO_3$, noble metals, and semiconductors, manufactured in a way that is similar to the above-mentioned example.

Figure 7:
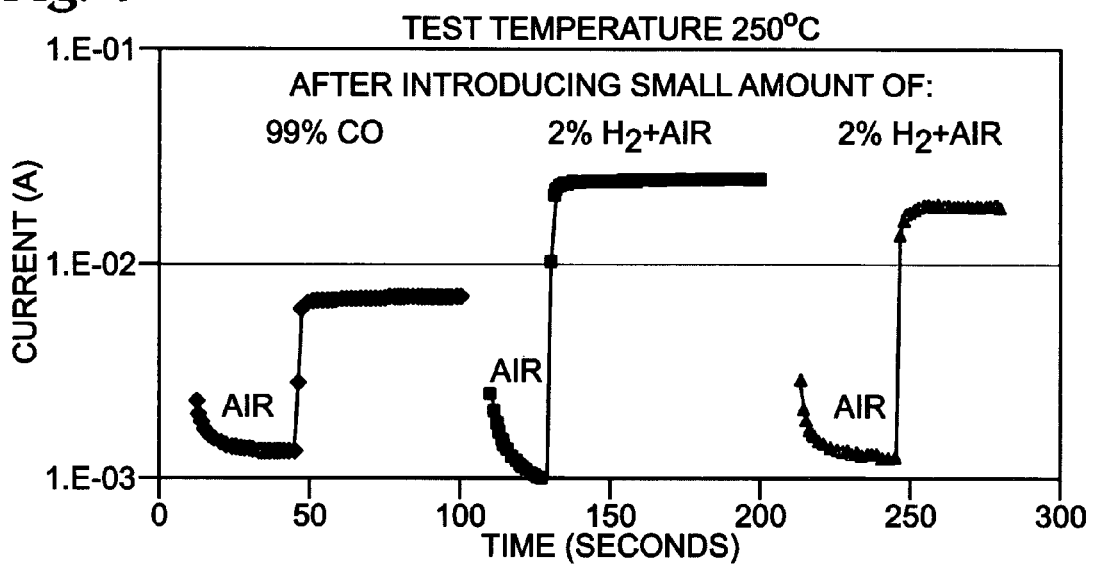
FIG. 7 is a graph depicting the response of a $TiO_2$ nanorod sensor to different gas environments.

FIG. 7 is a graph depicting the response of a $TiO_2$ nanorod sensor to different gas environments. Preliminary tests show that a $TiO_2$ nanorods gas sensor is responsive to small amount of CO and 2% $H_2$+air at a chamber pressure>100 torr. The testing temperature is 250° C.

Figure 8:
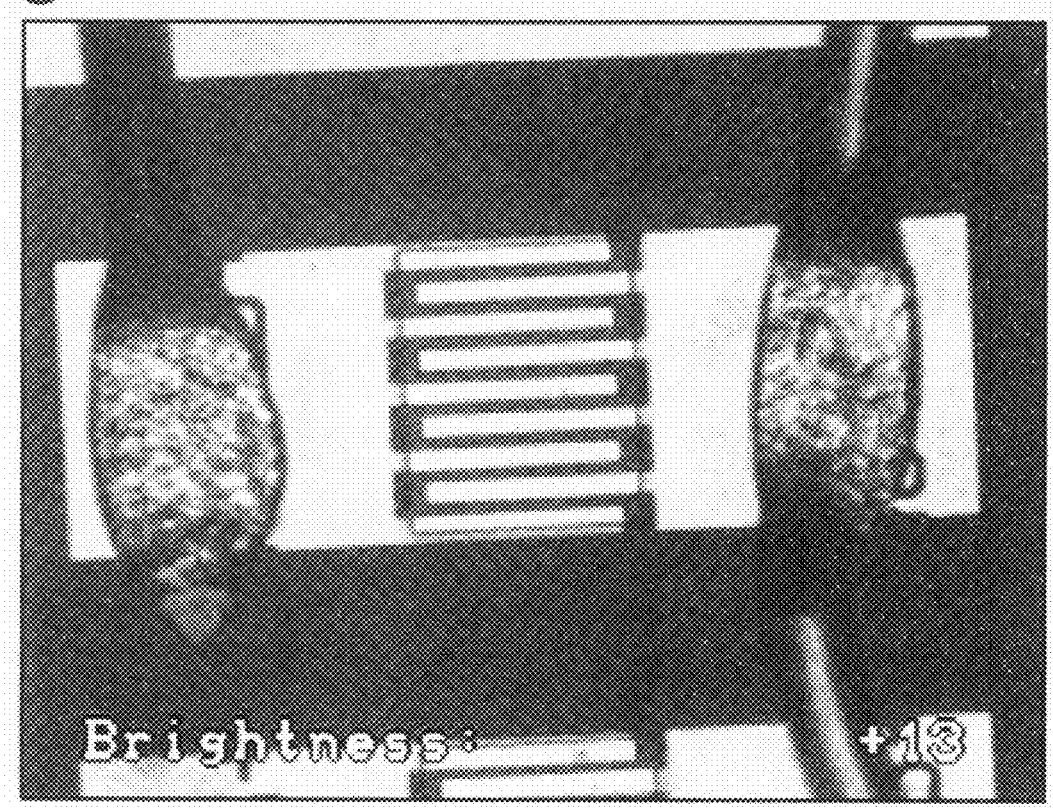
FIG. 8 is a plan view depicting an array of nanorod sensors.

FIG. 8 is a plan view depicting an array of nanorod sensors. As shown, the top electrode of parallel nanorod sensor sections are wire bonded together to form arrays. Since the nanorods structures underlying the top electrode sections are not conductive, and are used for just mechanical support, the array is not sensitive to damage that may occur to these nanorods are a result of the wire bonding process.

FIG. 9 is a flowchart illustrating a method for fabricating a nanorod sensor with a single plane of horizontally-aligned electrodes. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. The method starts at Step 900.

Step 902 provides a substrate such as Si, glass, plastic, or polyimide. If the substrate is Si, or some other non-insulator material, then Step 903 may be used to form a silicon dioxide layer overlying the substrate. Step 904 forms an intermediate electrode from a patterned bottom noble metal/Pt/Ti multilayered stack overlying a center region of the substrate. Step 906 forms $TiO_2$ nanorods. Step 908 forms a single plane of top electrodes overlying the $TiO_2$ nanorods. The method also forms a $TiO_2$ film interposed between the $TiO_2$ nanorods and electrodes. More explicitly, the $TiO_2$ film may be formed between the nanorods and the intermediate electrode, as in Step 905, formed between the nanorods and the single plane of top electrodes, as in Step 907, or between the nanorods and both the intermediate and top electrodes, in which case Steps 905 and 907 are both performed.

Forming the single plane of top electrodes in Step 908 includes substeps. Step 908a deposits a top noble metal/Pt/Ti multilayered stack overlying the $TiO_2$ nanorods. Step 908b selectively etches the top noble metal/Pt/Ti multilayered stack into top electrodes. More explicitly, Step 908b forms: a first top electrode overlying a first region of the $TiO_2$ film; a second top electrode overlying a second region of the $TiO_2$ film; and, an interdigital electrode overlying the intermediate electrode, interposed between the first and second top electrodes. The interdigital electrode has a first section connected to the first top electrode and a second section connected to the second top electrode. In one variation, interdigital fingers are formed and a boundary region separates the first section from the second section.

In one aspect, Step 905 forms a $TiO_2$ film interposed between the $TiO_2$ nanorods and the intermediate electrode, and selectively etching the noble metal/Pt/Ti multilayered stack in Step 908b further includes etching the $TiO_2$ film underlying the interdigital electrode boundary region.

In one aspect, forming the top and bottom noble metal/Pt/Ti multilayered stacks in Step 904 and 908a includes the following substeps (only the substeps for Step 904 are depicted). Step 904a forms a Ti layer having a thickness in a range of 10 to 100 nm. Step 904b forms a Pt layer overlying the Ti layer having a thickness in a range of 10 to 100 nm. Step 904c forms a noble metal layer overlying the Pt layer having a thickness of 100 nm to 1 micrometer. The noble metal may be Au, Ir, Pt, or Ru for example.

In another aspect, forming the $TiO_2$ nanorods in Step 906 includes growing $TiO_2$ nanorods at a substrate temperature in the range of 350 to 600° C. Forming the $TiO_2$ film in Steps 905 and 907 includes growing a rutile $TiO_2$ film at a substrate temperature in a range of 600 to 800° C. Alternately, forming the $TiO_2$ film in Step 905 and 907 includes growing an anatase phase $TiO_2$ film at a substrate temperature in a range of 250 to 350° C. If films are formed in both Step 905 and 907, they need not necessarily be the same phase. It should also be understood that that Steps 905, 906, and 907 may be formed as part of a continuous deposition process by merely changing the substrate temperature.

In one aspect, forming the $TiO_2$ film and $TiO_2$ nanorods (Steps 905, 906, and 907) includes establishing the following growth conditions:
creating a pressure in the range of 1 Torr to Atmosphere;
introducing a Ti isopropoxide $(Ti(OC_3H_7)_4)$ precursor;
maintaining precursor and transport lines at a temperature in the range of 20 to 80° C.;
introducing reaction gases such as $O_2$, Ar, or $N_2$; and,
introducing an Ar carrier gas.

In a different aspect, forming the $TiO_2$ film and $TiO_2$ nanorods in Steps 905, 906, and 907 includes establishing the following preconditions prior to establishing the growth conditions:
creating an initial pressure below 1 milliTorr;
introducing Ar until growth pressure is obtained; and,
introducing the carrier gas at a rate in a range of 10 standard cubic centimeters per minute (SCCM) and 100 SCCM.

A nanorod sensor and associated fabrication process have been presented. Specific structures, process details, and materials have been used to illustrate the invention. However, the invention is not necessarily limited to merely these examples. For example, similar processes and structures could be enabled using other metal oxides besides $TiO_2$. Other variations and embodiments of the invention will occur to those skilled in the art.

We claim:

1. A method for fabricating a nanorod sensor with a single plane of horizontally-aligned electrodes, the method comprising:
   providing a substrate;
   forming an intermediate electrode from a patterned bottom noble metal/Pt/Ti multilayered stack overlying a center region of the substrate;
   forming $TiO_2$ nanorods;
   forming a single plane of top electrodes overlying the $TiO_2$ nanorods; and,
   forming a $TiO_2$ film interposed between the $TiO_2$ nanorods and electrodes selected from a group consisting of the intermediate electrode, the top electrodes, and both the intermediate and top electrodes.

2. The method of claim 1 wherein forming the single plane of top electrodes includes:
   depositing a top noble metal/Pt/Ti multilayered stack overlying the $TiO_2$ nanorods; and,
   selectively etching the top noble metal/Pt/Ti multilayered stack into top electrodes.

3. The method of claim 1 wherein selectively etching the noble metal/Pt/Ti multilayered stack into top electrodes includes:
   forming a first top electrode overlying a first region of the $TiO_2$ film;
   forming a second top electrode overlying a second region of the $TiO_2$ film; and,
   forming an interdigital electrode overlying the intermediate electrode, interposed between the first and second top electrodes, having a first section connected to the first top electrode and a second section connected to the second top electrode.

4. The method of claim 3 wherein forming the interdigital electrode includes forming interdigital fingers and a boundary region separating the first section from the second section.

5. The method of claim 4 wherein forming the $TiO_2$ film includes forming a $TiO_2$ film interposed between the $TiO_2$ nanorods and the intermediate electrode; and,
   wherein selectively etching the noble metal/Pt/Ti multilayered stack into top electrodes further includes etching the $TiO_2$ film underlying the interdigital electrode boundary region.

6. The method of claim 1 wherein forming the $TiO_2$ nanorods includes growing $TiO_2$ nanorods at a substrate temperature in a range of 350 to 600° C.

7. The method of claim 1 wherein forming the $TiO_2$ film includes growing a rutile $TiO_2$ film at a substrate temperature in a range of 600 to 800° C.

8. The method of claim 1 wherein forming the $TiO_2$ film includes growing an anatase phase $TiO_2$ film at a substrate temperature in a range of 250 to 350° C.

9. The method of claim 1 wherein forming the $TiO_2$ film and $TiO_2$ nanorods includes establishing the following growth conditions:
   creating a pressure in a range of 1 Torr to Atmosphere;
   introducing a Ti isopropoxide ($Ti(OC_3H_7)_4$) precursor;
   maintaining precursor and transport lines at a temperature in a range of 20 to 80° C.;
   introducing reaction gases selected from a group consisting of $O_2$, Ar, and $N_2$; and,
   introducing an Ar carrier gas.

10. The method of claim 9 wherein forming the $TiO_2$ film and $TiO_2$ nanorods includes establishing the following preconditions prior to establishing the growth conditions:
    creating an initial pressure below 1 milliTorr;
    introducing Ar until growth pressure is obtained; and,
    introducing the carrier gas at a rate in a range of 10 standard cubic centimeters per minute (SCCM) and 100 SCCM.

11. The method of claim 1 wherein providing the substrate includes providing a substrate made from a material selected from a group consisting of Si, glass, plastic, and polyimide.

12. The method of claim 1 wherein providing the substrate includes providing a Si substrate; and,
    the method further comprising:
    forming a silicon dioxide layer overlying the substrate.

13. The method of claim 2 wherein forming the top and bottom noble metal/Pt/Ti multilayered stacks includes using a noble metal selected from a group consisting of Au, Ir, Pt, and Ru.

14. The method of claim 1 wherein forming the top and bottom noble metal/Pt/Ti multilayered stacks includes:
    forming a Ti layer having a thickness in a range of 10 to 100 nanometers (nm);
    forming a Pt layer overlying the Ti layer having a thickness in a range of 10 to 100 nm; and,
    forming a noble metal layer overlying the Pt layer having a thickness of 100 nm to 1 micrometer.

* * * * *